(12) United States Patent
Skorheim et al.

(10) Patent No.: US 11,899,839 B1
(45) Date of Patent: Feb. 13, 2024

(54) SYSTEM FOR MULTIMODAL MACHINE-AIDED COMPREHENSION ANALYSIS AND ASSISTANCE

(71) Applicant: HRL Laboratories, LLC, Malibu, CA (US)

(72) Inventors: Steven W. Skorheim, North Hills, CA (US); Tiffany Hwu, San Diego, CA (US)

(73) Assignee: HRL LABORATORIES, LLC, Malibu, CA (US)

( * ) Notice: Subject to any disclaimer, the term of this patent is extended or adjusted under 35 U.S.C. 154(b) by 0 days.

(21) Appl. No.: 17/965,566

(22) Filed: Oct. 13, 2022

Related U.S. Application Data

(60) Provisional application No. 63/315,500, filed on Mar. 1, 2022.

(51) Int. Cl.
  *G06F 3/01*   (2006.01)
  *A61B 3/113*  (2006.01)

(52) U.S. Cl.
  CPC .............. *G06F 3/015* (2013.01); *A61B 3/113* (2013.01)

(58) Field of Classification Search
  CPC ........... G06F 3/013; G06F 3/015; A61B 3/113
  USPC ....................................................... 345/156
  See application file for complete search history.

(56) References Cited

U.S. PATENT DOCUMENTS

| | | | | |
|---|---|---|---|---|
| 9,535,499 B2 * | 1/2017 | Lee | ........................ | G06F 3/0481 |
| 2007/0225577 A1 * | 9/2007 | Mathan | .................... | G06F 3/011 |
| | | | | 600/301 |
| 2020/0160744 A1 * | 5/2020 | Sipolins | .................. | G06F 3/015 |

OTHER PUBLICATIONS

Zareian, A., Karaman, S., & Chang, S.F. 020, August). Bridging knowledge graphs to generate scene graphs. In European Conference on Computer Vision, pp. 1-18 (606-623), Springer, Cham. (Year: 2020).*

Zareian, A., Karaman, S., & Chang, S. F. Aug. 2020). Bridging knowledge graphs to generate scene graphs. In European Conference on Computer Vision, pp. 1-18 (606-623), Springer, Cham.

Zareian, A., Karaman, S., & Chang, S. F. (Aug. 2020). Bridging knowledge graphs to generate scene graphs. In European Conference on Computer Vision, Supplementary Material, pp. 1-15, Springer, Cham.

(Continued)

*Primary Examiner* — Calvin C Ma
(74) *Attorney, Agent, or Firm* — TOPE-MCKAY & ASSOCIATES

(57) ABSTRACT

Described is a system for multimodal machine-aided comprehension analysis. The system can be implemented in an augmented reality headset that, in conjunction with a processor, generates an initial scene graph of a scene proximate the user. Items and labels are presented, with the headset tracking eye movements of the user as the user gazes upon the subject labels, item labels, and relationship labels. A resulting scene graph (having relationship triplets) is generated based on the eye movements of the user and an amount of time the user spends gazing upon each of the display components. A comprehension model is generated by estimating a user's comprehension of the relationship triplets, with a knowledge model being generated based on a known knowledge graph and the comprehension model. Cues are then presented to the user based on the comprehension and knowledge models to assist the user in their comprehension of the scene.

24 Claims, 10 Drawing Sheets

(56) References Cited

OTHER PUBLICATIONS

Yu, J., Chai, Y., Wang, Y., Hu, Y., & Wu, Q. (2020). CogTree: Cognition Tree Loss for Unbiased Scene Graph Generation. arXiv preprint arXiv:2009.07526, pp. 1-7.

Speer, Robert, and Catherine Havasi. "ConceptNet 5: A large semantic network for relational knowledge." The People's Web Meets NLP. Springer, Berlin, Heidelberg, 2013, pp. 161-176.

Bosselut, A., Rashkin, H., Sap, M., Malaviya, C., Celikyilmaz, A., & Choi, Y. (2019). Comet: Commonsense transformers for automatic knowledge graph construction. arXiv pre print arXiv:1906.05317, pp. 4762-4779.

Sun, Z., Wang, H., Wang, H., Shao, B., & Li, J. (2012). Efficient subgraph matching on billion node graphs. arXiv preprint arXiv:1205.6691, pp. 788-799.

\* cited by examiner

US 11,899,839 B1

SYSTEM FOR MULTIMODAL MACHINE-AIDED COMPREHENSION ANALYSIS AND ASSISTANCE

CROSS-REFERENCE TO RELATED APPLICATIONS

This application claims the benefit of and is a non-provisional patent application of U.S. Provisional Application No. 63/315,500, filed on Mar. 01, 2022, the entirety of which is hereby incorporated by reference.

BACKGROUND OF INVENTION (1) Field of Invention

The present invention relates to a comprehension assistance system and, more specifically, to a comprehension analysis and assistance system that uses eye tracking data to estimate a user's comprehension of a visual scene and generate cues to optimize the user's comprehension.

(2) Description Of Related Art

Human-machine cooperation is highly dependent on artificial intelligence systems to estimate the capabilities and needs of human users. While machine learning systems are capable of doing this, they can be overly specialized to certain tasks and take a great deal of data to train. Existing cognitive models, such as ACT-R, have been used to create cognitive tutoring systems. Compared to pure machine learning systems, the use of cognitive modeling can reduce training and data requirements by incorporating information on human tendencies and prior knowledge. However, these models are also specialized to specific tasks and mostly provide feedback using a fixed collection of modalities. They have rarely been used to specifically model the communicative state of the human. Separately, eye tracking hardware has been used extensively in psychophysics to determine the attention targets of individual users. While eye gaze has been used to aid machine tasks such as image captioning, it has not been incorporated into a cognitive model that can be easily used for a variety of tasks.

Thus, a continuing need exists for a multimodal machine-aided comprehensive analysis and assistance system that incorporates a cognitive model to allow the system to be quickly applied to different tasks and users.

SUMMARY OF INVENTION

The present disclosure provides a system for multimodal machine-aided comprehension analysis. Using one or more processors, the system performs a series of operations, including generating an initial scene graph of a scene proximate a user based on an image of the scene, the initial scene graph having one or more subjects and objects, with subject labels, item labels, and relationship labels; tracking eye movements of the user as the user gazes upon the subject labels, item labels, and relationship labels; generating a resulting scene graph based on the eye movements of the user and an amount of time the user spends gazing upon each of the subject labels, item labels and relationship labels, the resulting scene graph connecting the subject labels, item labels and relationship labels as relationship triplets; generating a comprehension model by estimating a user's comprehension of the relationship triplets in the image based on the user's gaze data; and generating a knowledge model based on a known knowledge graph and the comprehension model, the knowledge model specifying the user's background knowledge level and comprehension level. Further, in some aspects, the system performs an operation of generating a cue and presenting the cue, via an augmented reality headset, to the user.

In another aspect, if the user has comprehension below a predetermined comprehension threshold and background knowledge above a predetermined background knowledge threshold, then the cue is a visual cue.

In yet another aspect, if the user has comprehension below a predetermined comprehension threshold and background knowledge below a predetermined background knowledge threshold, then the cue is a dialog-based cue.

In another aspect, the comprehension model is generated by determining a comprehension value for each possible triplet in the scene graph, based on $$Comprehension_{Relationship} = \frac{T_1 + T_2}{C_1 + T_T},$$

where $T_1$ denotes a gaze time looking at an object in the relationship triplet, $T_2$ denotes a gaze time looking at a subject in the relationship triplet, $C_1$ denotes a constant calibration value, and $T_T$ denotes a shortest time between looking at one item before another item.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
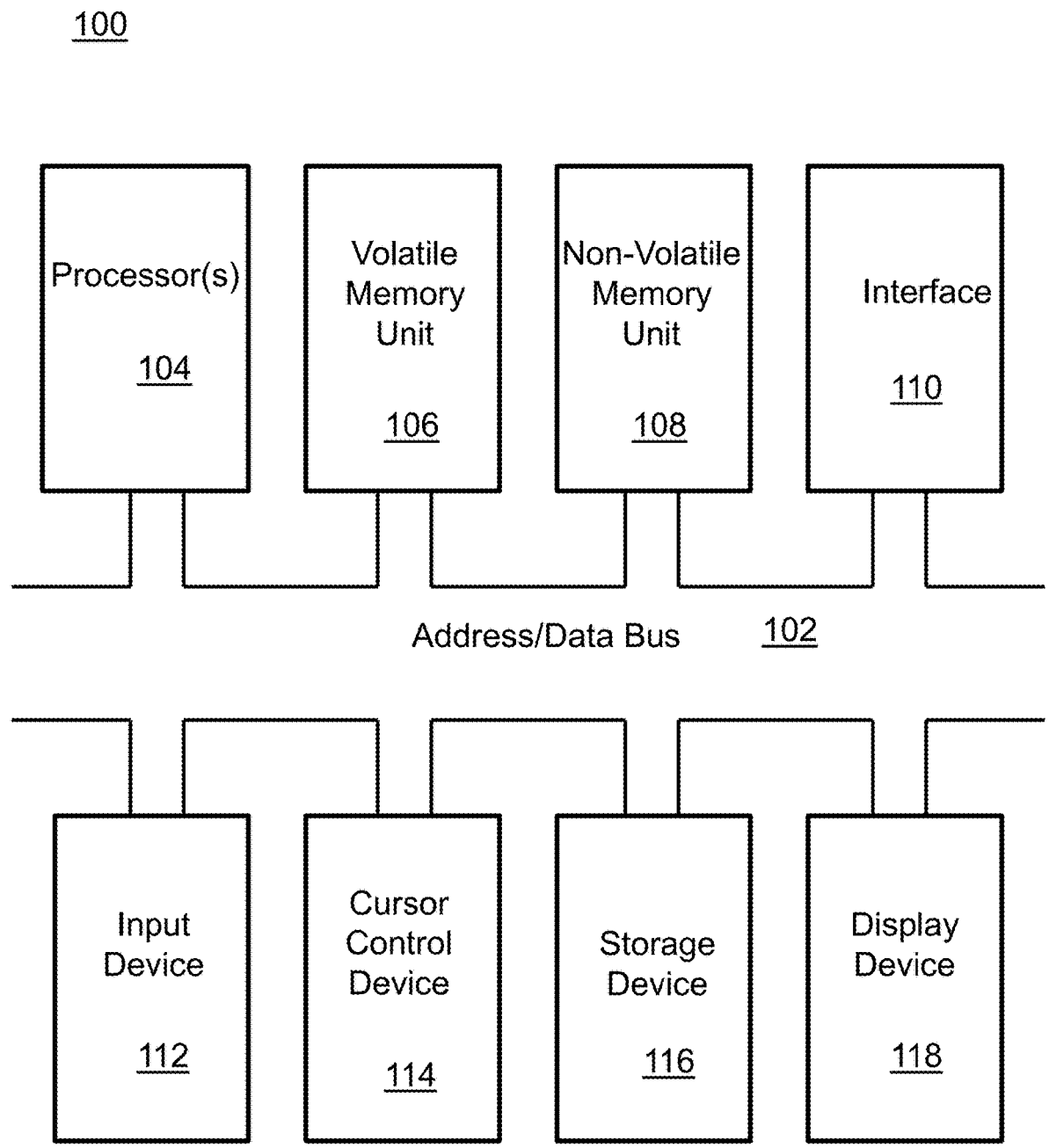
FIG. 1 is a block diagram depicting the components of a system according to various embodiments of the present invention.

The present invention relates to a comprehension assistance system and, more specifically, to a comprehension analysis and assistance system that uses eye tracking data to estimate a user's comprehension of a visual scene and generate cues to optimize the user's comprehension. The following description is presented to enable one of ordinary skill in the art to make and use the invention and to incorporate it in the context of particular applications. Various modifications, as well as a variety of uses in different applications, will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112(f). In particular, the use of "step of" or "act of" in the claims herein is not intended to invoke the provisions of 35 U.S.C. 112(f).

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) List Of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Zareian, A., Karaman, S., & Chang, S. F. (2020, Aug.). Bridging knowledge graphs to generate scene graphs. In *European Conference on Computer Vision* (pp. 606-623). Springer, Cham.
2. Yu, J., Chai, Y,, Wang, Y., Hu, Y., & Wu, Q. (2020). CogTree: Cognition Tree Loss for Unbiased Scene Graph Generation. *arXiv preprint arXiv:*2009.07526.
3. Speer, Robert, and Catherine Havasi. "ConceptNet 5: A large semantic network for relational knowledge." *The People's Web Meets NLP.* Springer, Berlin, Heidelberg, 2013. 161-176.
4. Bosselut, A., Rashkin, H., Sap, M., Malaviya, C., Celikyilmaz, A., & Choi, Y. (2019). Comet: Commonsense transformers for automatic knowledge graph construction. *arXiv preprint arXiv:*1906.05317.
5. Sun, Z., Wang, H., Wang, H., Shao, B., & Li, J. (2012). Efficient subgraph matching on billion node graphs. *arXiv preprint arXiv:*1205.6691.

(2) Principal Aspects

Various embodiments of the invention include three "principal" aspects. The first is a system for multi-modal machine-aided comprehension analysis and assistance. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein. In various aspects, the computer system 100 can be embodied in any device(s) that operates to perform the functions as described herein as applicable to the particular application, such as a desktop computer, a mobile or smart phone, a tablet computer, a computer embodied in a mobile platform, or any other device or devices that can individually and/or collectively execute the instructions to perform the related operations/processes.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA) or any other processing component operable for performing the relevant operations.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology. Further, one or more processors 104 (or devices) can be associated with one or more associated memories, where each associated memory is a non-transitory computer-readable medium. Each associated memory can be associated with a single processor 104 (or device), or a network of interacting processors 104 (or devices).

In one aspect, the computer system 100 may include an input device 112 coupled with the address/data bus 102, wherein the input device 112 is configured to communicate information and command selections to the processor 104. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 104. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
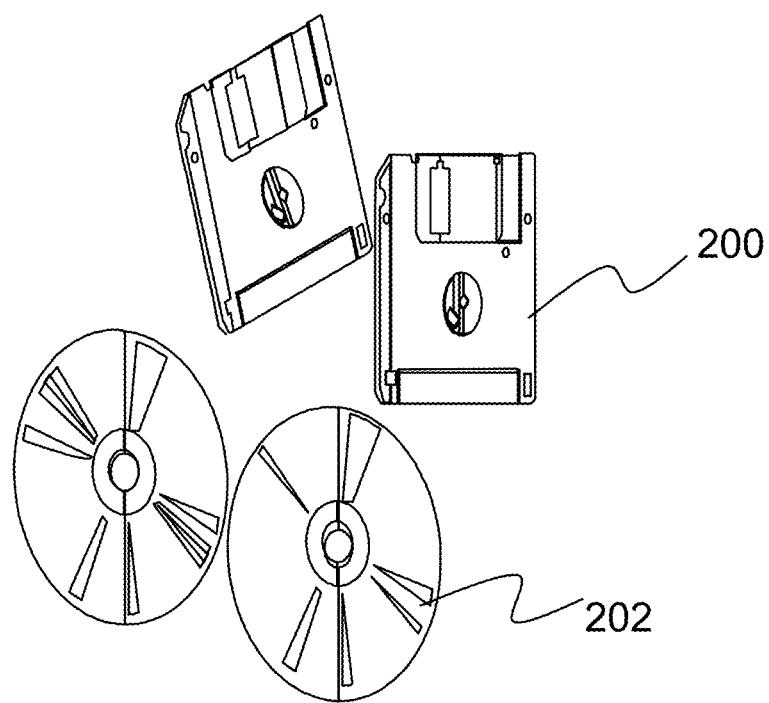
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

The present disclosure provides a system and method for modeling a human user's comprehension of a task and assisting the user by communicating cues in modalities appropriate to the situation. While the user is performing a task, the system uses eye tracking data to monitor the user's awareness of relationships between task-relevant items. This information is combined with scene graphs and knowledge graphs of task-relevant information to generate a model of the user's current understanding. This model is then used to select optimal forms of assistance to assist the user in completing the task. When the model predicts low comprehension of vital information, helpful cues are communicated through visual prompts and/or spoken dialogue. Over time, the system collects information on what the user has learned, which can then be used to model the user's background knowledge for improved assistance.

Through collecting information on user learning and modeling background knowledge, the system is operable for improving human task performance. In particular, the system makes informed decisions about which mode of communication to use for a given piece of information, choosing modalities that optimize efficiency of learning and avoid unnecessary distractions. The universal format of scene graphs allows the system to interface with common databases and communication systems. Further, the additional use of knowledge graphs allows the system to represent common knowledge on the relationships between items to estimate the user's understanding beyond what is present in the scene.

The system can be implemented for use in the development of automated training programs and machine-aided task assistance. Specific applications include enhanced flight checklists for pilots and ground crew, vehicle navigation assistance, coordination of manufacturing processes, task guidance in maintenance tasks, and advanced warning systems. In some applications, the system is integrated into physical machines to assist humans with practical tasks. When implemented on physical hardware, it may be part of a physical machine involved in controlling the machine. Specific details are provided below.

(4) Specific Details Of Various Embodiments

While artificial intelligence (AI) systems have greatly expanded their capabilities, many tasks contain elements that will require human intelligence for a long time to come. This disclosure provides a system that will assist a human with a task, optimizing learning and performance while minimizing distractions. Currently, systems tend to rely on scripted assistance or cues that depend on a single event, such as a warning. Rather than interleaving AI with human actions and assessments in the loop, current systems switch rigidly between human and machine control without interaction between the two. The system of the present disclosure creates a model of the user's cognitive state based on eye tracking data, and a scene graph and knowledge graph of task-relevant information. Using this information, the system estimates the user's comprehension of a visual scene. If comprehension of a certain relationship is thought to be low due to the user not seeing a pair of related items, the system visually cues the user to that pair of items. The system also tracks the user's knowledge of relevant relationships outside of the visible scene. If the user has looked at a pair of items but the system predicts that the user has little knowledge of how they are related, the system will provide a brief dialog-based explanation.

As noted above, the system and described method is widely applicable to many tasks. However, as a non-limiting example and to demonstrate the use of the system and method, this disclosure describes an embodiment involving a generic visual understanding task. Visual understanding is often used in surveillance, navigation, and maintenance applications. The visual search task requires the user to look at an image and connect words, such as with arrows, in order to describe the relationships described in the image.

Figure 3:
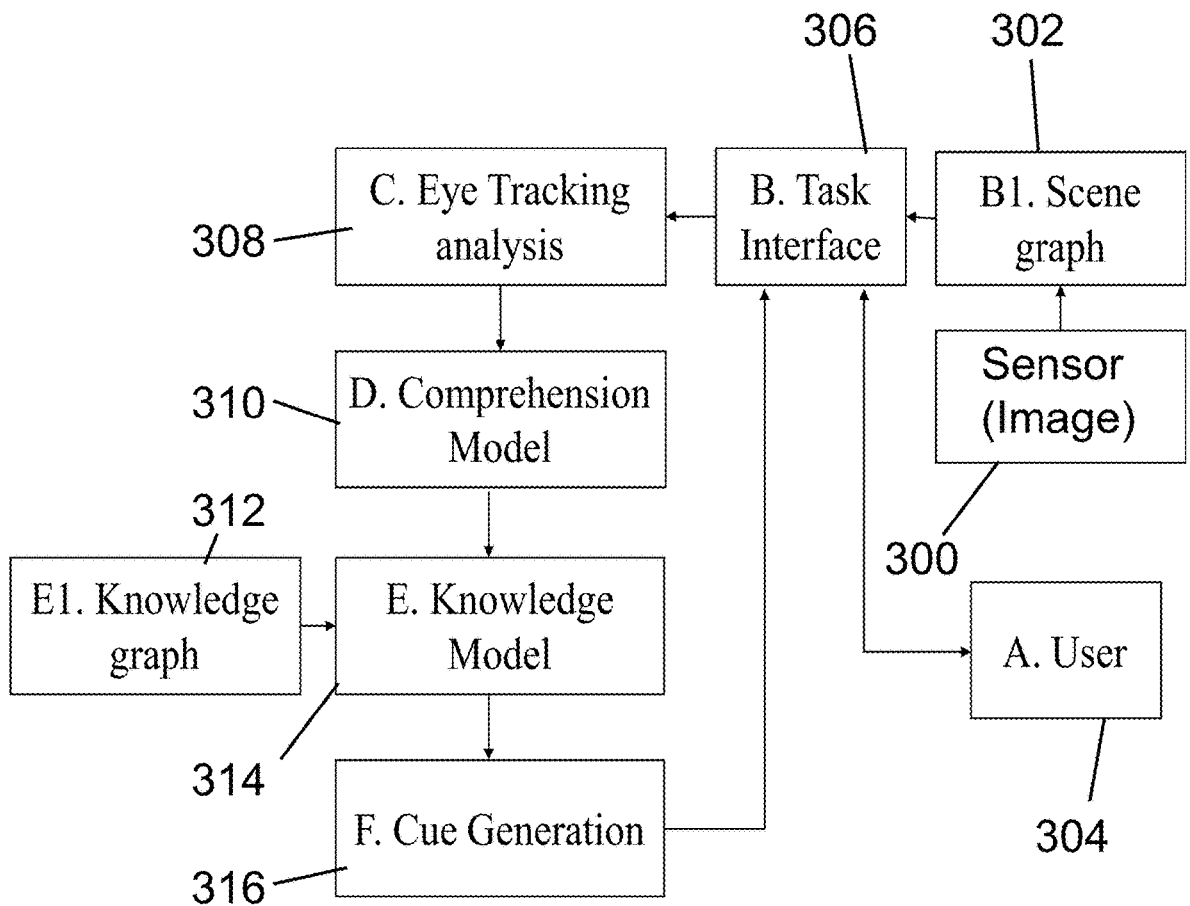
FIG. 3 is a flowchart depicting a process by which the system incorporates task and scene data with eye tracking data to model a user's comprehension and accumulates an understanding of the user's knowledge and capabilities with related sub tasks for cue generation to aid the user in completing the task.

An overview of the system components and process are shown in FIG. 3. The system uses a sensor (e.g., camera, lidar, etc.) that generates an image 300 of a scene proximate the user 304. As used herein, a user 304 is a person performing a task that receives cues from the system and works with the task interface 306. A scene graph 302 is generated (via a scene graph generation module) that can be presented to the user 304 via the task interface 306 or other display. The system then collects data from the user 304 via the user's interaction with a task interface 306. That information is analyzed and used to inform the comprehension and knowledge models. The output of these models then determines the most useful cues to give back to the user 304. Although not limited thereto, a specific example of a system embodying this invention uses an augmented reality headset to guide a user in a tool arrangement task.

Eye tracking analysis 308 is employed that incorporates task and scene data with eye tracking data to model of the user's comprehension 310 and accumulates an understanding of the user's knowledge 314 (from a knowledge graph 312) and capabilities with related sub tasks. This information is then used for cue generation 316 to aid the user 304 in completing the task. Further details are provided below.

In one aspect, the user's 304 task is to view an image 300 on an external display and to construct a scene graph 302 of that image 300 by observing the relationships of items in a scene. The graph 302 is constructed on the display, adjacent to the image 300. Items and relationships are depicted as boxes, and the user 304 connects the boxes by arrows (or other markers) to indicate how the items relate to each other. If any mistakes are made by the user 304, the user 304 is alerted and must correct the mistakes. The user 304 is scored based upon the number of errors and the amount of time taken. In other embodiments, the actual task may occur in a physical environment while the interface may be implemented on a display within an augmented reality headset with a head-mounted camera for scene perception. Further, in such an aspect, eye tracking data may be collected using gaze detection hardware included within the headset.

The scene graph 302 is a set of relationship triplets consisting of subject, object, and relationship and can be visualized in a graphical representation. The graph 302 describes an entire visible scene according to all of the present items and their relationships. Each item has a class label and corresponding bounding box marking its location in the image 300. Pre-existing scene graph generation techniques can be employed to identify relationship triplets from camera images, such as GB-Net and CogTree (see the List of Incorporated Literature References, Literature Reference Nos. 1 and 2, respectively). Current scene graph generation techniques often have low accuracy (~40%), which is due to accumulated error from the multiple processing stages of object segmentation, classification, and scene graph generation. Object classification can be improved by training models specifically for the target task domain. The set of possible relationship triplets can also be reduced to a smaller domain. For instance, many tasks could use a simple set of spatial relationships (e.g., "to the left of", "above") for describing ideal item placements.

In some aspects, the image 300 consists of a photograph of a naturalistic scene displayed on a monitor (or headset, etc.), which is then assessed by the user 304 who is tasked with understanding the scene. Alternatively, images 300 may also come from streamed video input from a head-mounted camera as the user performs a task of tool arrangement. The image 300 feeds into the scene graph 302 generation module. During scene graph 302 generation, important items found in the image 300 are identified and marked by bounding boxes. For example, GB-Net and CogTree identify the items and generate the bounding boxes.

As noted above, the system employs eye tracking analysis 308 using an appropriate eye tracking module (with relevant hardware/software) to generate the scene that the user is currently looking at. Further, the eye tracking module monitors which items within the scene the user is looking at and how long the user is looking at each one. This relies upon existing and well-established hardware for extracting gaze coordinates over time. A non-limiting example of such hardware and software include Smart Eye AI-X as produced by Smart Eye, located at Första Långgatan 28B, 413 27, Gothenburg, Sweden. To determine the total gaze time spent looking at an item, the bounding boxes of items from the most recently generated scene graph generation are provided as candidate items and locations. If the focal point of gaze lies within the bounding box of any item, the total time spent looking at a specific item is increased. This is captured in the following formula:

$$Gaze_{item}(t) = \begin{cases} Gaze_{item}(t-1) + 1 & \text{if focal point in } obj \text{ bounding box} \\ Gaze_{item}(t-1) & \text{otherwise} \end{cases}$$

The term t denotes the timestep of interest. Gaze time is therefore measured in timesteps. Time intervals between time steps are determined by the sampling rate of the eye tracking device. Time steps may be reset to 0 periodically if the particular task is only concerned with recent eye gaze behavior as opposed to eye gaze throughout the entire task. For instance, if the scene changes, the timestep can be reset.

In some cases, a gaze point may be located inside multiple bounding boxes. In such a case, the total gaze time for each of the relevant bounding boxes is increased. There may also be cases in which there are multiple items of the same class. The object detection algorithm used in scene graph generation should assign unique identifiers to each individual item and ensure that duplicate items are assigned consistent identifiers from one frame to the next.

Comprehension analysis 310 is performed using a comprehension model that estimates the user's current understanding of each scene graph triplet in the image based on gaze data. If the user looks directly from an object to a subject, the comprehension model estimates a high probability (e.g., greater than 50%, or any other predetermined value) that the user understands the relationship between them. The following equation describes a comprehension value for each possible triplet in the scene graph:

$$Comprehension_{Relationshi} = \frac{T_1 + T_2}{C_1 + T_T}$$

$T_1$—Gaze time looking at object in the relationship triplet $T_2$—Gaze time looking at subject in the relationship triplet $C_1$—A predetermined constant calibration value(e.g., 1.0, etc.)

$T_T$—Shortest time between looking at one item before the other

The knowledge graph 312 has the same format as the scene graph 302, but describes common knowledge relationships about items in the scene. These relationships may not actually be present in the scene, but capture the beliefs of the majority of users. The knowledge graph 312 can be obtained from task-specific datasets. For tasks based on everyday scene understanding, an existing knowledge database such as ConceptNet may be used (see Literature Reference No. 3). For more domain-specific tasks, a task-specific dataset may consist of an instruction manual or video. Relationships may be manually extracted from these databases, or an automated approach such as COMET may be used (see Literature Reference No. 4).

The knowledge model 314 has the same format as the comprehension model 310, but stores averaged values of all item relationships observed over all observations of the user over time. Initial values for knowledge of relationships are initialized from the knowledge graph 312 in order to help generate the knowledge model 314. For example, the knowledge model 314 incorporates the confidence of the knowledge of relationships using a scalar representation. In FIG. 8B, for example, confidence is pictorially represented using the thickness of the relationship edges.

Given the knowledge model 314, cues can be generated with a cue generator 316. The cue generator 316 determines whether cueing information related to a triplet in the scene graph 302 would be helpful and decides which modality to present the cue. If the knowledge model 314 of the user 304 indicates a poor understanding of a relationship, a dialog cue is deployed to convey the information. If the comprehension model 310 indicates that the user 304 has likely not observed a certain relationship, they are visually cued. Visual cues can be shown or displayed to the user 304 rapidly and may point out important connections that the user 304 has overlooked, while dialog-based cues can give more detailed information and fill in gaps in the user's 304 background knowledge. The generated cues are then provided to the Task Interface 306, which displays the cues to the user 304.

Figure 4:
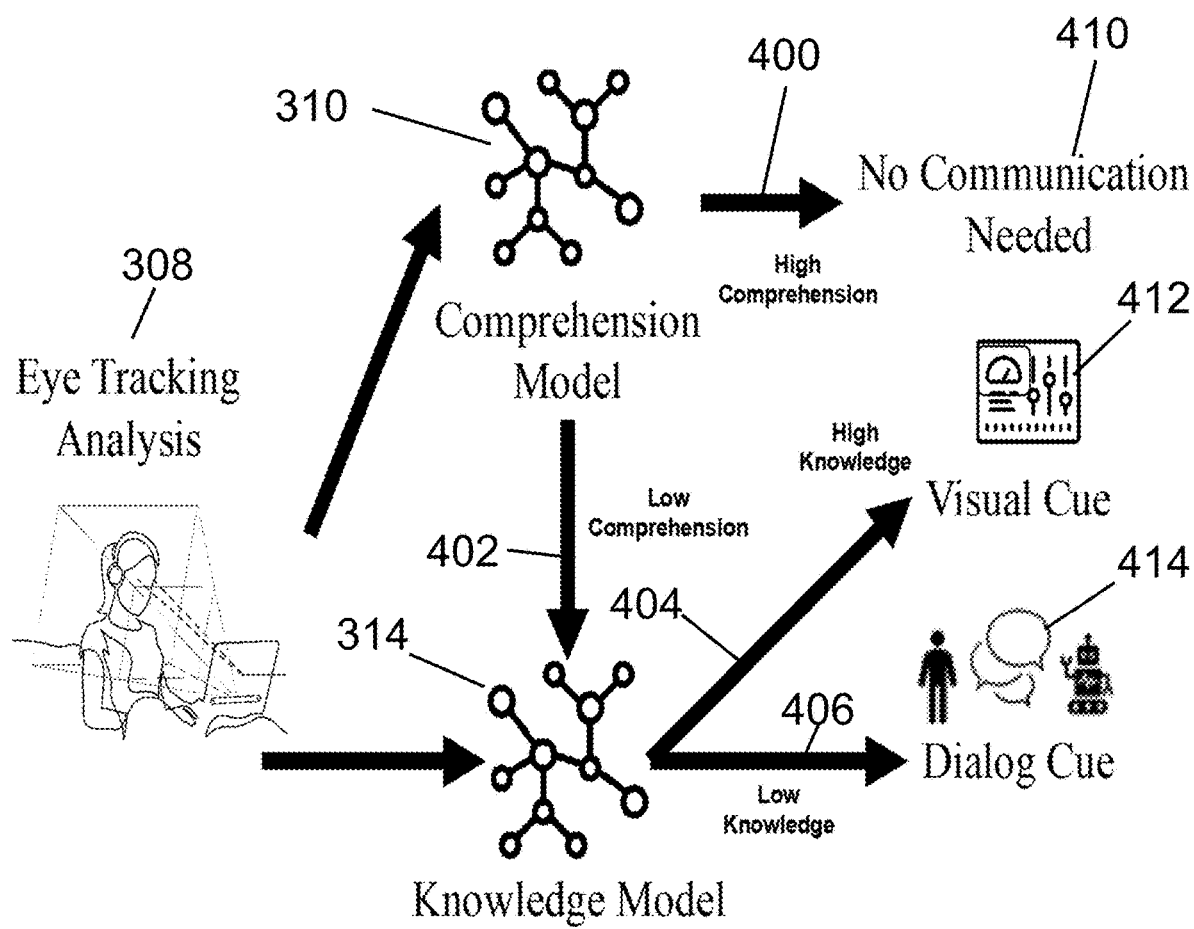
FIG. 4 is an illustration depicting components used in cue generation.
Figure 5:
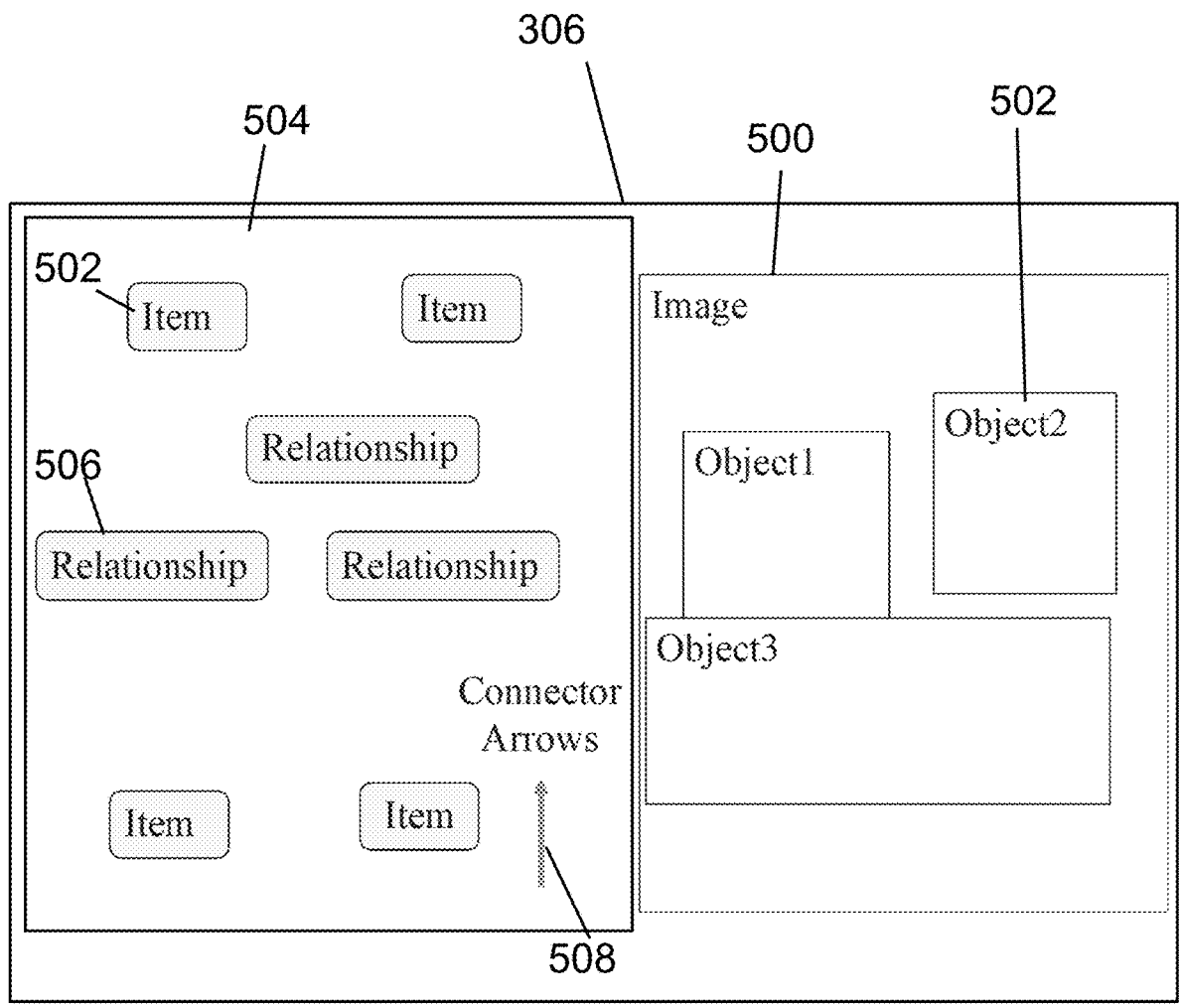
FIG. 5 is an illustration depicting a generic example of a visual reasoning task as used with the system.

For further understanding, FIG. 4 is a flowchart illustrating how the outputs of cognitive modeling are used in the cue generation component to determine which modality of communication is appropriate. For any triplet in the scene graph, the user's gaze data (via eye tracking 308) is used to generate comprehension 310 and knowledge 314 scores. If the user has high comprehension 400 (e.g., greater than 50%, 60%, or any other predetermined value designated as "high") of the relationship, no communication is needed 410. If the user has low comprehension 402 (e.g., probability less than 50%, 40%, etc., or any other predetermined value designated as "low") but high background knowledge 404 (e.g., greater than 0.5., 0.6, or any other predetermined value designated as "high"), a visual cue is given 412. If the user has low comprehension 402 and low background knowledge 406 (e.g., less than 0.5., 0.4, or any other predetermined value designated as "low"), a dialog-based cue is given 414. In one example embodiment, the determination of whether a comprehension or knowledge value is high or low can be found by applying thresholds to determine the value as being above or below a predetermined value designated as high or low An example of this process is depicted in FIG. 5, which depicts a generic example of a visual reasoning task used with the system. In this example, a user is presented an image 500 of a scene that includes a plurality of objects or items 502. Using the task interface 306 and relationship controls 504, the user tries to lay out the relationships between the items 502 in an image 504. For example, the user can place connector arrows 508 and define relationships 506 between the items 502 in the image 500 using a touch screen and/or mouse. When the system estimates low comprehension of an important relationship, it gives the user a visual or dialog-based cue to help them comprehend it.

To further demonstrate the process, the system was tested on a visual reasoning task in which a specific image and scene graph was used that the user was expected to construct. The comprehension model, knowledge model, and cue generation were assessed. These aspects are described in turn below.

Figure 6:
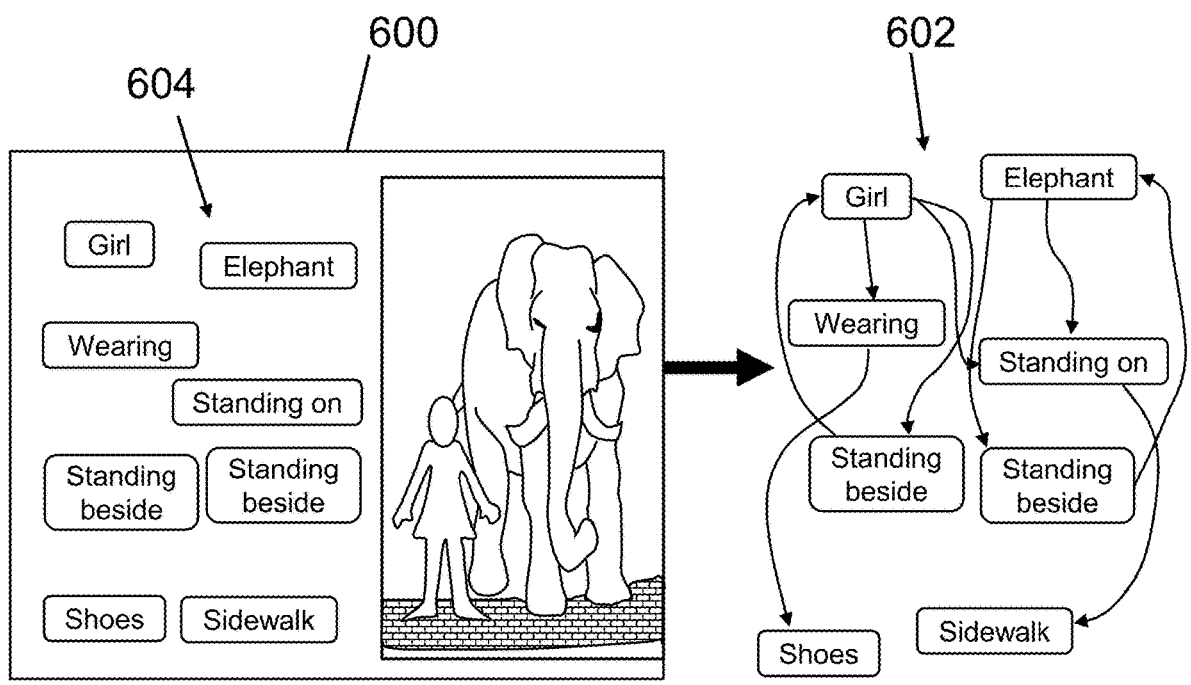
FIG. 6 is an illustration depicting an example scene graph before and after being connected by the user.
Figure 7:
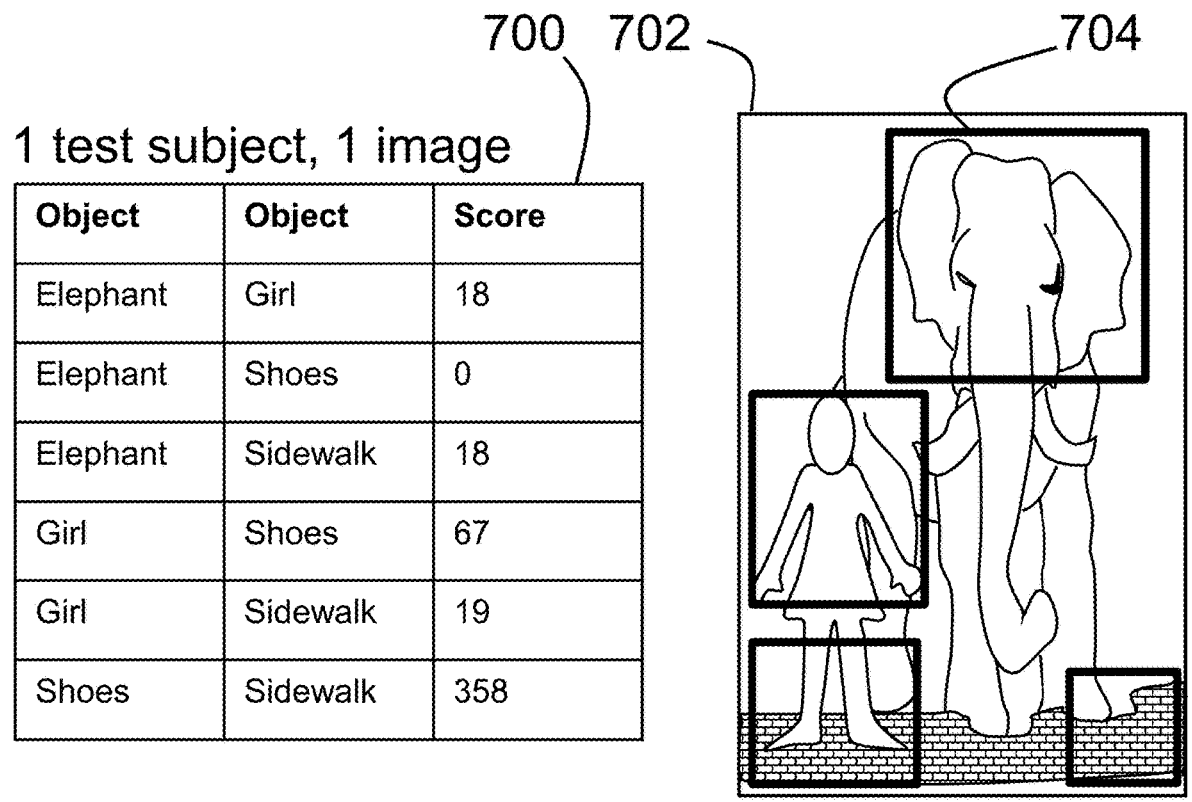
FIG. 7 is an illustration depicting a scene for gaze detection and corresponding results using the system according to various aspects of the present invention.

In a test of the comprehension model, a user was asked to perform the task with an eye tracker to determine the gaze times and duration for items in the image. The task interface 600 is shown in FIG. 6 with the resulting scene graph 602. The initial scene graph 604 is shown with the items before being connected by the user, while the resulting scene graph 602 is depicted after arrows were used to connect the time boxes while the users' time and eye movements were recorded. In this example and as shown in FIG. 7, the results 700 of the image 702 show that the user clearly associated the girl with her shoes and the shoes to the sidewalk, while other relationships were only briefly considered. The user was determined to be looking at an item if her gaze was detected within the bounding box 704 in the image. Comprehension scores were calculated using the above methods. A score of above 40 indicates good comprehension of the relationship. These results seem to match the intuitive sense of the important connections the user made.

For each given task, such as the visual reasoning task presented here, a corresponding knowledge graph can be constructed to capture background knowledge on objects in the scene. For instance, it is common knowledge that people wear shoes and that people stand on sidewalks. For the image provided in FIG. 7, the knowledge graph could consist of the information as depicted in FIG. 8A and the related knowledge model as shown in FIG. 8B.

Figure 8A:
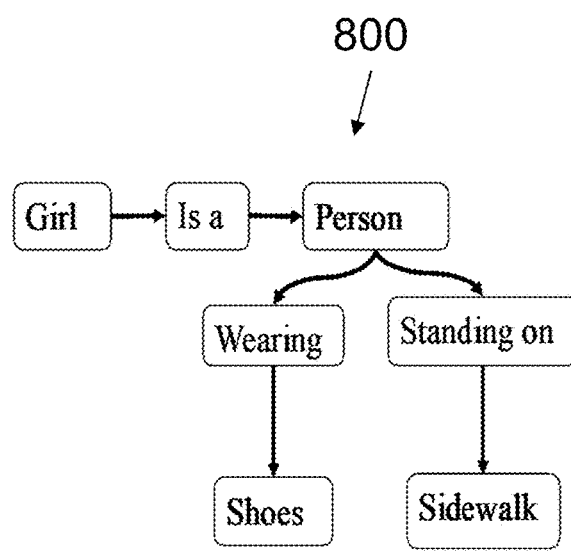
FIG. 8A is an example knowledge graph of items relevant to the scene graph depicted in FIG. 6.
Figure 8B:
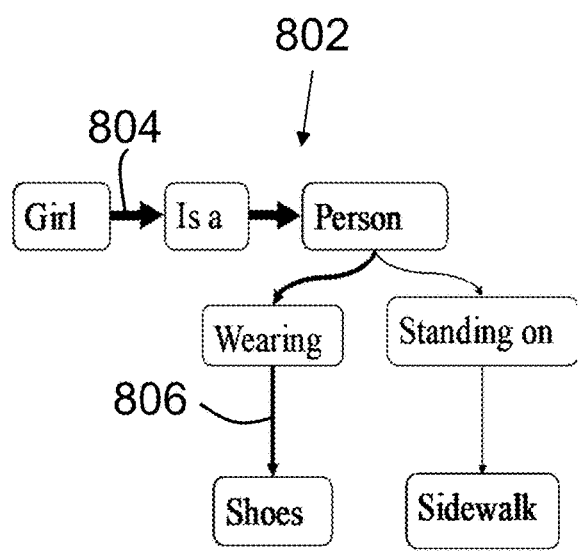
FIG. 8B is an example knowledge model of the user, depicting varying values for each relationship in the knowledge graph representing a specific user's knowledge.

In the example as shown in FIG. 8A, three relationships are captured in the knowledge graph 800: "Girl is a person", "Person wearing shoes", and "Person standing on sidewalk". Such relationships can be drawn from public knowledge databases such as ConceptNet (see Literature Reference No. 3), which consist of commonly known relationships between items. In this specific example, the concept "Shoes are worn by people" exists in ConceptNet. However, there may be other commonsense relationships not captured by the database, for which a more domain-specific database would need to be processed. For instance, an instructional manual may describe a desired configuration of items (e.g. "screwdriver should be to the left of the pliers"). A transform for automated knowledge graph construction (such as COMET (see Literature Reference No. 4)) can then be used extract relationship triplets from the text to capture this knowledge.

As shown in FIG. 8B, the knowledge model 802 of a specific user is expressed in the same format as this knowledge graph, except that each relationship is encoded with a numerical strength value representing the user's understanding of that specific relationship. As noted above, the numerical strength value can be represented pictorially using the thickness of the relationship edges, such that a thicker edge 804 reflects a higher numerical strength value than a thinner edge 806. Matching the elements of a scene graph from eye tracking analysis to the elements of a knowledge graph can be achieved by searching for the existence of each scene graph relationship triplet within the entire knowledge graph. However, in some cases it may be necessary to represent the context of scene graph relationships. For instance "Girl wearing shoes" may only be relevant in the outdoor context. In this case, matching the scene graph to the knowledge graph may require more advanced graph representation and/or subgraph matching techniques (see, for example, Literature Reference No. 5). If no observational data of the user exists, the knowledge model is an exact copy of the relevant parts of the knowledge graph with all numeral strength values set to a uniform value. Over time, the knowledge model may be modified to fit the user's knowledge according eye tracking data and interactions with the interface. An example of using eye tracking data to modify the knowledge model would be if a relationship such as "person wearing shoes" exists, but the user has viewed 100 images and never looked at a person and shoes in succession. An example of an interaction with the interface would be that a user often does not make the correct connection between the box for "person" and the box for "shoes" when performing a collection of 100 tasks containing this relationship. Since the construction of a knowledge model requires observations over a longer period of time, the example user test did not provide actual knowledge values.

After updating the comprehension model and knowledge model, a cue can be generated to guide the user in an aspect of the task. For the relationship, "person wearing shoes", if the comprehension is high, no communication is performed. If comprehension is low and knowledge is low, the sentence "The person is wearing shoes" would be played to the user. If comprehension is low and knowledge is high, the girl and shoes would be highlighted with a visual overlay.

The task described thus far may be extended to applications in scene understanding. As can be appreciated by those skilled in the art, there are other applications in which the system can be employed. As a non-limiting example, an alternative task involves tool placement. In this task, a scene graph describes the spatial placement of tools on a table, with relationship triplets such as "tape above wrench". The task requires the user to arrange tools in an optimal spatial configuration while interacting with an augmented reality (AR) headset. A non-limiting example of such a headset is HoloLens 2, which is a pair of mixed reality smart glasses developed and manufactured by Microsoft Corporation, located in Redmond, Wash., .U.S.A..

Figure 9:
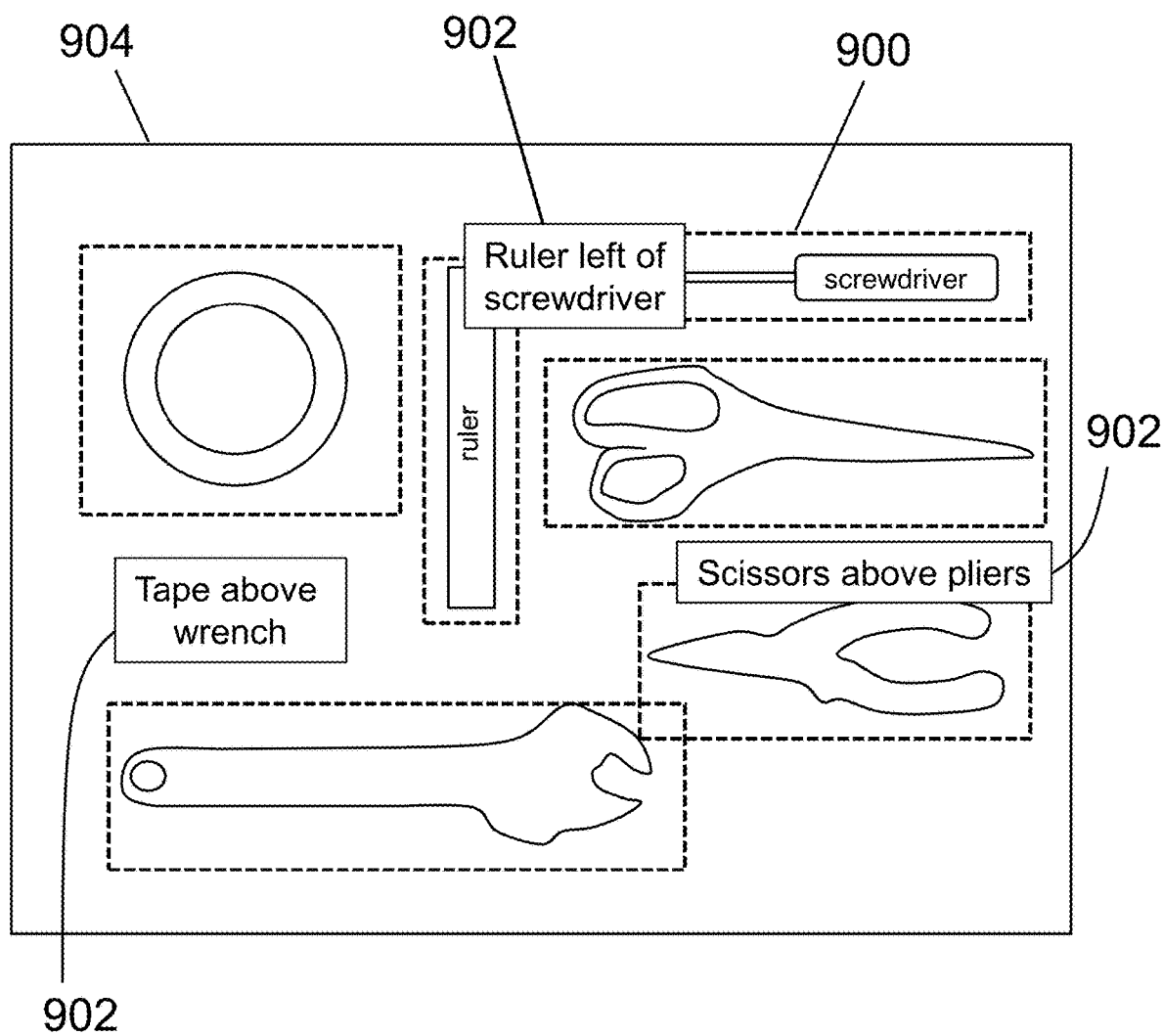
FIG. 9 is an illustration depicting a tool arrangement task.

In this task, the images are streamed from a head-mounted display on the headset. For example, FIG. 9 shows an illustrative example of a single frame capture 904 from the headset with bounding boxes 900 (depicted in dashed lines) and relationship triplets 902 overlaid. From instruction manuals, a knowledge graph may contain relationship triplets 902 describing the optimal arrangement of tools for a task (e.g. "tape above wrench"). The eye tracking hardware included in the headset is capable of tracking the user's gaze. Since the scene graph presented here consists of only spatial relationships, scene graph generation has an accuracy of near 100% when items are unobscured. In such a task, knowledge of optimal spatial configurations can be drawn from an instructional diagram or text. Built-in speech-to-text and text-to-speech functionalities allow for multimodal cue generation, such as in-situ visual overlays and dialog. The user can then use generated cues to arrange the items in an optimal configuration.

Figure 10:
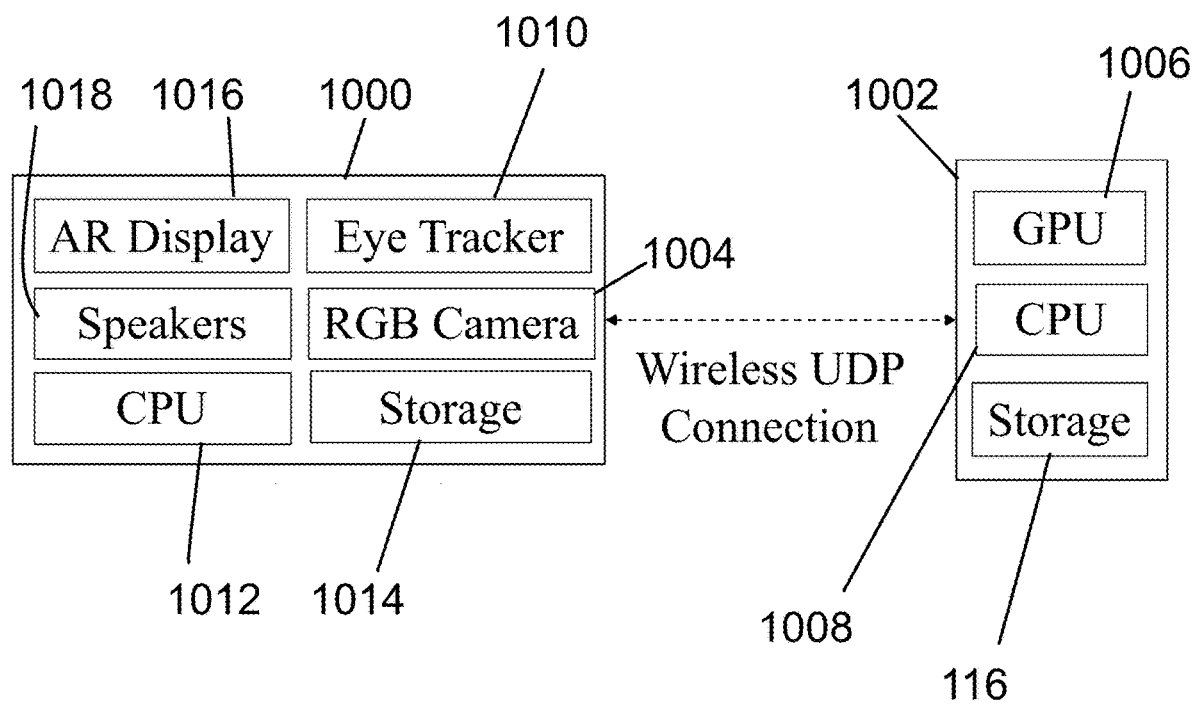
FIG. 10 is an illustration depicting an example device layout for a tool arrangement class task.

FIG. 10 provides an example of a device layout that is capable of embodying this invention. In one aspect, all of the processing components as described herein (or any combination thereof) can be completed entirely on the augmented reality headset. However, in another aspect and as shown in FIG. 10, each component of FIG. 3 can be implemented using the devices of an augmented reality headset 1000 and an external server 1002. The user wears a headset 1000 (e.g., Hololens 2), while the task interface is implemented via the subcomponents of the headset 1000. A stream of images is recorded from the head-mounted red-green-blue (RGB) camera 1004 on the headset 1000 and sent to an external server 1002 via a user datagram protocol (UDP) wireless connection. The external server 1002 is analogous to the server depicted in FIG. 1 as element 100, with the display device 118 and interface 110 being provided by the headset 1000. Note that in this example, the headset 1000 similia includes any processor, memory, and/or other components as necessary to perform the requisite functions as performed by the headset 1000 component. Also in this example, the external server 1002 performs scene graph generation, which requires a graphics processing unit (GPU) 1006 for running neural network algorithms and a computer processing unit (CPU) 1008 for coordinating the receiving of frames and other auxiliary functions necessary for running the neural network algorithms. For clarity, the GPU 1006 and CPU 1008 are contained within the one or more processors as also depicted as element 104 in FIG. 1. The GPU 1006 Parameters, such as neural network weights, are stored in the storage 116 of the external server 1002. Generated scene graphs are sent back to the Hololens headset 1000. The eye tracking device 1010 within the headset 1000 tracks gaze points and matches them with item bounding boxes from the scene graph. The comprehension model is run by the CPU 1012 on the Hololens headset 1000, with the model being stored on storage 1014 of the headset 1000. The knowledge output is also implemented on the Hololens headset 1000. However, the knowledge graph itself is stored on the server 1002. The server GPU 1006 or CPU 1008 extracts relevant portions of the knowledge graph to send to the headset 1000 via the UDP connection. Lastly, cue generation is run on the CPU 1012 of the Hololens device 1000 (or any other computing device that can communicate with the display or headset), and cues are presented to the user in a multimodal fashion, with visual cues being shown on the AR display 1016 and audio cues played through the speakers 1018 on the headset 1000.

To provide an example of cue generation, suppose that the user is tasked with arranging tools in a desired spatial layout, with the layout described in a manual. The user has one error in the arrangement. The comprehension model determines that the user already has high comprehension of what the error is, as the eye tracking output has calculated that the user has already gazed at the items in question. The cue generation component therefore avoids generating unnecessary cues, as it would be distracting to the user.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for multimodal machine-aided comprehension analysis, the system comprising:
   one or more processors and associated memory, the memory being a non-transitory computer-readable medium having executable instructions encoded thereon, such that upon execution of the instructions, the one or more processors perform operations of:
   generating an initial scene graph of a scene proximate a user based on an image of the scene, the initial scene graph having one or more subjects and objects, with subject labels, item labels, and relationship labels;
   tracking eye movements of the user as the user gazes upon the subject labels, item labels, and relationship labels;
   generating a resulting scene graph based on the eye movements of the user and an amount of time the user spends gazing upon each of the subject labels, item labels and relationship labels, the resulting scene graph connecting the subject labels, item labels and relationship labels as relationship triplets;
   generating a comprehension model by estimating a user's comprehension of the relationship triplets in the image based on the user's gaze data;
   generating a knowledge model based on a known knowledge graph and the comprehension model, the knowledge model specifying the user's background knowledge level and comprehension level; and
   generating a cue and presenting the cue to the user.

2. The system as set forth in claim 1, wherein the cue is generated and presented to the user via an augmented reality headset.

3. The system as set forth in claim 2, wherein if the user has comprehension below a predetermined comprehension threshold and background knowledge above a predetermined background knowledge threshold, then the cue is a visual cue.

4. The system as set forth in claim 3, wherein if the user has comprehension below a predetermined comprehension threshold and background knowledge below a predetermined background knowledge threshold, then the cue is a dialog-based cue.

5. The system as set forth in claim 4, wherein the comprehension model is generated by determining a comprehension value for each possible triplet in the scene graph, based on $$Comprehension_{Relationship} = \frac{T_1 + T_2}{C_1 + T_T},$$

where $T_1$ denotes a gaze time looking at an object in the relationship triplet, $T_2$ denotes a gaze time looking at a subject in the relationship triplet, $C_1$ denotes a constant calibration value, and $T_T$ denotes a shortest time between looking at one item before another item.

6. The system as set forth in claim 1, wherein if the user has comprehension below a predetermined comprehension threshold and background knowledge above a predetermined background knowledge threshold, then the cue is a visual cue.

7. The system as set forth in claim 1, wherein if the user has comprehension below a predetermined comprehension threshold and background knowledge below a predetermined background knowledge threshold, then the cue is a dialog-based cue.

8. The system as set forth in claim 1, wherein the comprehension model is generated by determining a comprehension value for each possible triplet in the scene graph, based on $$Comprehension_{Relationshi} = \frac{T_1 + T_2}{C_1 + T_T},$$

where $T_1$ denotes a gaze time looking at an object in the relationship triplet, $T_2$ denotes a gaze time looking at a subject in the relationship triplet, $C_1$ denotes a constant calibration value, and $T_T$ denotes a shortest time between looking at one item before another item.

9. A computer implemented method for multimodal machine-aided comprehension analysis, the method comprising an act of:
   causing one or more processors to execute instructions encoded on a non-transitory computer-readable medium, such that upon execution, the one or more processors perform operations of:
   generating an initial scene graph of a scene proximate a user based on an image of the scene, the initial scene graph having one or more subjects and objects, with subject labels, item labels, and relationship labels;
   tracking eye movements of the user as the user gazes upon the subject labels, item labels, and relationship labels;
   generating a resulting scene graph based on the eye movements of the user and an amount of time the user spends gazing upon each of the subject labels, item labels and relationship labels, the resulting scene graph connecting the subject labels, item labels and relationship labels as relationship triplets;
   generating a comprehension model by estimating a user's comprehension of the relationship triplets in the image based on the user's gaze data;
   generating a knowledge model based on a known knowledge graph and the comprehension model, the knowledge model specifying the user's background knowledge level and comprehension level; and
   generating a cue and presenting the cue to the user.

10. The method as set forth in claim 9, wherein the cue is generated and presented to the user via an augmented reality headset.

11. The method as set forth in claim 10, wherein if the user has comprehension below a predetermined comprehension threshold and background knowledge above a predetermined background knowledge threshold, then the cue is a visual cue.

12. The method as set forth in claim 11, wherein if the user has comprehension below a predetermined comprehension threshold and background knowledge below a predetermined background knowledge threshold, then the cue is a dialog-based cue.

13. The method as set forth in claim 12, wherein the comprehension model is generated by determining a comprehension value for each possible triplet in the scene graph, based on $$Comprehension_{Relationship} = \frac{T_1 + T_2}{C_1 + T_T},$$

where $T_1$ denotes a gaze time looking at an object in the relationship triplet, $T_2$ denotes a gaze time looking at a subject in the relationship triplet, $C_1$ denotes a constant calibration value, and $T_T$ denotes a shortest time between looking at one item before another item.

14. The method as set forth in claim 9, wherein if the user has comprehension below a predetermined comprehension threshold and background knowledge above a predetermined background knowledge threshold, then the cue is a visual cue.

15. The method as set forth in claim 9, wherein if the user has comprehension below a predetermined comprehension threshold and background knowledge below a predetermined background knowledge threshold, then the cue is a dialog-based cue.

16. The method as set forth in claim 9, wherein the comprehension model is generated by determining a comprehension value for each possible triplet in the scene graph, based on $$Comprehension_{Relationship} = \frac{T_1 + T_2}{C_1 + T_T},$$

where $T_1$ denotes a gaze time looking at an object in the relationship triplet, $T_2$ denotes a gaze time looking at a subject in the relationship triplet, $C_1$ denotes a constant calibration value, and $T_T$ denotes a shortest time between looking at one item before another item.

17. A computer program product for multimodal machine-aided comprehension analysis, the system comprising:
   a non-transitory computer-readable medium having executable instructions encoded thereon, such that upon execution of the instructions by one or more processors, the one or more processors perform operations of:
   generating an initial scene graph of a scene proximate a user based on an image of the scene, the initial scene graph having one or more subjects and objects, with subject labels, item labels, and relationship labels;
   tracking eye movements of the user as the user gazes upon the subject labels, item labels, and relationship labels;
   generating a resulting scene graph based on the eye movements of the user and an amount of time the user spends gazing upon each of the subject labels, item labels and relationship labels, the resulting scene graph connecting the subject labels, item labels and relationship labels as relationship triplets;
   generating a comprehension model by estimating a user's comprehension of the relationship triplets in the image based on the user's gaze data;
   generating a knowledge model based on a known knowledge graph and the comprehension model, the knowledge model specifying the user's background knowledge level and comprehension level; and
   generating a cue and presenting the cue to the user.

18. The computer program product as set forth in claim 17, wherein the cue is generated and presented to the user via an augmented reality headset.

19. The computer program product as set forth in claim 18, wherein if the user has comprehension below a predetermined comprehension threshold and background knowledge above a predetermined background knowledge threshold, then the cue is a visual cue.

20. The computer program product as set forth in claim 19, wherein if the user has comprehension below a predetermined comprehension threshold and background knowledge below a predetermined background knowledge threshold, then the cue is a dialog-based cue.

21. The computer program product as set forth in claim 20, wherein the comprehension model is generated by determining a comprehension value for each possible triplet in the scene graph, based on $$Comprehension_{Relationship} = \frac{T_1 + T_2}{C_1 + T_T},$$

where $T_1$ denotes a gaze time looking at an object in the relationship triplet, $T_2$ denotes a gaze time looking at a subject in the relationship triplet, $C_1$ denotes a constant calibration value, and $T_T$ denotes a shortest time between looking at one item before another item.

22. The computer program product as set forth in claim 17, wherein if the user has comprehension below a predetermined comprehension threshold and background knowledge above a predetermined background knowledge threshold, then the cue is a visual cue.

23. The computer program product as set forth in claim 17, wherein if the user has comprehension below a predetermined comprehension threshold and background knowledge below a predetermined background knowledge threshold, then the cue is a dialog-based cue.

24. The computer program product as set forth in claim 17, wherein the comprehension model is generated by determining a comprehension value for each possible triplet in the scene graph, based on $$Comprehension_{Relationship} = \frac{T_1 + T_2}{C_1 + T_T},$$

where $T_1$ denotes a gaze time looking at an object in the relationship triplet, $T_2$ denotes a gaze time looking at a subject in the relationship triplet, $C_1$ denotes a constant calibration value, and $T_T$ denotes a shortest time between looking at one item before another item.

* * * * *